(12) United States Patent
Kirsh et al.

(10) Patent No.: US 11,612,703 B2
(45) Date of Patent: Mar. 28, 2023

(54) PUSH CONNECTOR FOR VAPE CARTRIDGES

(71) Applicant: Vapor Dosing Technologies, Inc., Venice, CA (US)

(72) Inventors: Yisroel Kirsh, Venice, CA (US); Akiva Wagner, Woodmere, NY (US); Robert Stephen Walter Bates, Venice, CA (US)

(73) Assignee: Vapor Dosing Technologies, Inc., San Francisco, CA (US)

( * ) Notice: Subject to any disclaimer, the term of this patent is extended or adjusted under 35 U.S.C. 154(b) by 0 days.

(21) Appl. No.: 17/635,996

(22) PCT Filed: Dec. 11, 2019

(86) PCT No.: PCT/US2019/065644
§ 371 (c)(1),
(2) Date: Feb. 16, 2022

(87) PCT Pub. No.: WO2021/034341
PCT Pub. Date: Feb. 25, 2021

(65) Prior Publication Data
US 2022/0271466 A1 Aug. 25, 2022

(30) Foreign Application Priority Data

Aug. 16, 2019 (WO) ............... PCT/US2019/046853

(51) Int. Cl.
*H01R 13/26* (2006.01)
*A24F 40/42* (2020.01)
(Continued)

(52) U.S. Cl.
CPC ............ *A61M 11/042* (2014.02); *A24F 40/10* (2020.01); *A24F 40/20* (2020.01); *A24F 40/42* (2020.01);
(Continued)

(58) Field of Classification Search
CPC ...... H01R 13/26; A61M 11/042; A24F 40/42; A24F 40/40
See application file for complete search history.

(56) References Cited

U.S. PATENT DOCUMENTS

2014/0041655 A1 2/2014 Barron et al.
2015/0216232 A1 8/2015 Bless et al.
(Continued)

FOREIGN PATENT DOCUMENTS

WO WO-2020037226 A1 * 2/2020 ............. A24F 40/10
WO WO-2021034341 A1 * 2/2021 ............. A24F 40/50

OTHER PUBLICATIONS

The Original DabCap—Universal Vape to Bong Adapter (Cali Connected) [online] (retrieved from Internet on Jan. 29, 2020) < URL: https://caliconnected.com/products/the-original-dabcap?variant=8231848607797 >; Nov. 15, 2018.

*Primary Examiner* — Hae Moon Hyeon
(74) *Attorney, Agent, or Firm* — Finn IP Law

(57) ABSTRACT

The present invention provides a connector for push-connecting a cartridge containing vaporizable material, such as a 510-cartridge, to a power-supplying device. The connector includes a housing containing electrical contacts, a cartridge-receiving end for receiving a conductive end of the cartridge, and a flexible, preferably silicone, ring connected to the cartridge receiving end of the housing for retaining the conductive end of the cartridge inserted therethrough against the electrical contacts. The ring is preferably part of a silicon boot that houses the housing.

16 Claims, 11 Drawing Sheets

(51) Int. Cl.
| | |
|---|---|
| A61M 11/04 | (2006.01) |
| G16H 40/67 | (2018.01) |
| G16H 20/13 | (2018.01) |
| A24F 40/53 | (2020.01) |
| A24F 40/65 | (2020.01) |
| A24F 40/10 | (2020.01) |
| A24F 40/20 | (2020.01) |
| A24F 40/57 | (2020.01) |
| A24F 40/51 | (2020.01) |
| A24F 40/485 | (2020.01) |
| A24F 40/50 | (2020.01) |
| H01R 13/62 | (2006.01) |
| H01R 13/652 | (2006.01) |
| H01R 13/73 | (2006.01) |
| H01R 43/26 | (2006.01) |
| H01R 103/00 | (2006.01) |

(52) U.S. Cl.
CPC ............ *A24F 40/485* (2020.01); *A24F 40/50* (2020.01); *A24F 40/51* (2020.01); *A24F 40/53* (2020.01); *A24F 40/57* (2020.01); *A24F 40/65* (2020.01); *G16H 20/13* (2018.01); *G16H 40/67* (2018.01); *H01R 13/26* (2013.01); *H01R 13/62* (2013.01); *H01R 13/652* (2013.01); *H01R 13/73* (2013.01); *H01R 43/26* (2013.01); *A61M 2205/127* (2013.01); *A61M 2205/13* (2013.01); *A61M 2205/3317* (2013.01); *A61M 2205/3331* (2013.01); *A61M 2205/3344* (2013.01); *A61M 2205/3368* (2013.01); *A61M 2205/3386* (2013.01); *A61M 2205/3584* (2013.01); *A61M 2205/3653* (2013.01); *A61M 2205/50* (2013.01); *A61M 2205/502* (2013.01); *A61M 2205/8206* (2013.01); *A61M 2207/00* (2013.01); *A61M 2230/42* (2013.01); *H01R 2103/00* (2013.01)

(56) References Cited

U.S. PATENT DOCUMENTS

| | | |
|---|---|---|
| 2016/0015104 A1 | 1/2016 | Edwards et al. |
| 2016/0286859 A1 | 10/2016 | Liu |
| 2016/0360788 A1 | 12/2016 | Wang |
| 2017/0162979 A1 | 6/2017 | Liu |
| 2018/0020734 A1 | 1/2018 | Angstead et al. |
| 2018/0064166 A1 | 3/2018 | Arnel et al. |
| 2021/0346617 A1* | 11/2021 | Wagner ................... A24F 40/20 |

\* cited by examiner

PUSH CONNECTOR FOR VAPE CARTRIDGES

RELATED APPLICATIONS

This application is a U.S. national stage of PCT International Patent Application No. PCT/US2019/065644 having an international filing date of Dec. 11, 2019, which claims the benefit of International Patent Application No. PCT/US2019/046853 having an international filing date of Aug. 16, 2019. All of the above-identified applications are incorporated by this reference in their entireties for all purposes as if fully set forth herein.

TECHNICAL FIELD

The present invention relates generally to the field of vaporization systems and in particular to systems and methods for connecting vaporizer cartridges to batteries.

BACKGROUND

Systems and methods for connecting electric-powered, and typically rechargeable battery-powered, vaporizers (often simply called "batteries") to vaporizer cartridges or pods, in order to, upon activation, heat and vaporize the liquid material contained in the cartridge or pod for inhaling are well known. While there exists several proprietary cartridge or pod plus battery systems, the standard "510 thread" cartridge/battery system (or simply "510 thread system") predominates. "510" refers to the size of the thread of the screw on a cartridge, namely 10 threads at 0.5 mm per thread with an M7 threading. Conventionally, a 510 system works by simply screwing a metal, 510-threaded male end of a vape cartridge into a mating female, 510-thread connector of the battery. When properly secured and in good operating condition, a center pin in the battery connector, serving as a positive pole, makes good, electrically-conductive contact with the center ring or pin in the cartridge, with the outer 510 thread of the cartridge screwed into the mating 510 thread of the battery serving as the ground of the electrical circuit. The 510-thread standard has led to the proliferation of cartridge makers (of both pre-filled, disposable and user-refillable types) and independent battery makers, the buyer knowing that any 510 vape cartridge will connect to any "510 battery."

Indeed, numerous 510 battery configurations have evolved in recent years. A common battery design is the simple "pen-style" system, whereby the threaded end of a standard 510 cartridge simply screws into a mating female end of a rechargeable, typically push button-activated, pen-shaped battery having an outer circumference that is often the same as or close to the circumference of a standard vape cartridge. Another increasingly-popular battery design takes a more matchbox-like shape, and connects with the 510 end of the cartridge by inserting into a tubular-shaped cavity in the battery housing itself. This configuration can be more attractive than pen-style batteries for a number of reasons. These batteries (a) can take many different form factors, including ones that can discreetly fit in one hand even with a connected cartridge; (b) can have large power-storing capacities for longer use between recharging; and (c) can offer better control of the delivery of the vape to the user, with the inclusion of all sorts of smart electronics, read-outs, etc.

Unfortunately, the user experience with any of these conventional types of vape cartridge/battery systems has been less than ideal. The very nature of the 510-thread design requires screwing a cartridge onto the power-supplying device, or battery unit. This ran be cumbersome and even burdensome, especially for people with limited finger mobility or hand strength. It also leaves open the possibility of overtightening a cartridge into the battery, a known problem that ran damage both the cartridge and the battery device, and can make it difficult to separate them without an external tool.

Moreover, and perhaps most critically from the perspective of the rechargeable battery maker and user, irrespective of the style or design, it is important that the female connector in the battery device make consistently reliable electrical connection with the positive and ground contacts of any of the myriad, $3^{rd}$-party, 510 cartridges sold on the market. But ensuring this is not trivial. 510 connections have been known to degrade with use and even become disconnected and wholly inoperable due to a number of known reasons. One common reason is leakage of vaporizable material from poorly-made or defective cartridges that ends up blocking or mucking up the positive contacts of the batteries and ruining the electrical connection. Once leakage from an inserted cartridge occurs and sets into the female battery connector, unless the connection terminal can be and is thoroughly cleaned with a cleaner such as rubbing alcohol, the battery device may be garbage. Another cause of electrical disconnection from cartridges is severe over-tightening, which may push the positive cartridge contact too high vertically to then make connection again. A user will require a tool, or fingernails, to delicately pull the positive contact pin down to make connection again. Practically, most consumers will throw away the supposed defective battery and/or cartridge.

Various solutions to the 510-threaded connection problems have been proposed with varying degrees of success. For example, CCell™ has designed an alternative battery configuration for connecting 510 cartridges with its Palm™ device (and other similar models) that converts the 510-screw connection to a magnetic connection. It accomplishes this by supplying with the device a metal, ring-shaped adapter tube with ferromagnetic characteristics that is not inherent to the metal of the male 510 thread. The user must thread this ring onto the male 510 thread of the cartridge, which becomes a threadless extension of the cartridge ground. The ring and cartridge assembly are then slid or dropped into a female, tubular, magnetically-attracting terminal featuring a pogo-pin center contact on the device side.

Unfortunately, this is a less than ideal solution. For one, an additional, easily misplaced, small adapter ring that screws onto the cartridge must be supplied and used in order to make electrical connection. Moreover, when the cartridge is empty and ready to be replaced (in the case of disposable cartridges), the adaptor must be unscrewed from the previous cartridge and screwed onto the replacement cartridge. It is common for users to accidentally dispose of these adapters and require purchasing replacements. These extra steps are both inconvenient (screwing pieces on and off cartridges) and wasteful, and make the battery useless without an adaptor.

Accordingly, what is needed is a simple, user-friendly solution for connecting a vape cartridge to a power supply device. The solution would solve the 510-connection problems by eliminating the shortcomings inherent in the conventional screw-on screw-off system/process as well as the attempted solutions to these problems. Such a solution would ideally eliminate the need for a separate a component or adaptor to make the connection. What is further needed is a long-lasting connector design built into a power supplying device for easy and repetitive connecting and disconnecting vape cartridges to the power-supplying device.

SUMMARY

The present invention meets these needs by disclosing an improved system and connector for connecting a cartridge into a power supplying device that solves the aforementioned problems and more.

The Quick-Snap™ connector system of the present invention provides a simple solution to the shortcomings of standard threaded and magnetized cartridge connectors, as well as other attempted solutions in the art. The invention is a new device, or connector, and system, preferably designed in a cartridge-receiving cavity of a vaporizer power supplying device (or "battery" for shorthand) that makes connecting standard, unmodified 510-threaded cartridges (and even non-threaded cartridges) having vaping material therein as easy as pushing them into the connector ("push-connecting") and makes removing cartridges as easy as pulling them out of the connector with sufficient, but not too much, force. The Quick-Snap™ connector assembly, or connector, may be installed in a housing of a power-supplying device which may provide vertical support walls to reduce horizontal movement of the cartridge inserted therein. As designed for 510 cartridges, within the assembly, a silicone ring may replace the female 510 connector threads on the connector and its inner circumference grips the male 510 threads/stem on the cartridge. This silicone ring may create an inward compression on the male 510 threaded stem and catches the uppermost (closest to the mouthpiece) lip of the male 510 threads, thereby tending to create an airtight seal and prevent the cartridge from accidental electrical disconnection from the device.

In one embodiment, the Quick-Snap™ connector assembly, or connector, may comprise a molded silicone boot with an inserted, internal skeleton, or housing. The housing maintains the structure of the hollow cavity within the silicone boot and preferably contains two or more electrically-conductive contacts within it. The positive contact may travel vertically through or near the center of the housing and preferably is "spring-loaded," or has "give," in order to accommodate a range of positive contact, or pin, heights in different cartridge designs. A dome shaped end of the positive contact of the inventive connector may be used in order to allow the connector to make good connection with a variety of shapes and sizes of cartridge positive contacts, and a hole in its center may allow for air to flow through it and up through the cartridge. The ground(s) may also spring loaded, pushing with horizontal force against the cartridge thread region. A positive and ground tab preferably protrude out of the bottom of the internal housing and thread through slits in the silicone boot, in order to allow for easy soldering with a printed circuit board (PCB). Preferably, a port is also featured in the silicon boot allowing for a buffer seal between the PCB and a pressure sensor. The entire assembly may thus create a sealed, inert airflow channel and may isolate all potentially harmful electrical components (and manufacturing related chemicals/residue) from the pathway to the user's lungs. This focus on separation of airflow and electrical components allows for the connector of the present invention to be a medical grade solution for vapor inhalation.

Furthermore, the present invention provides a novel connector for push-connecting a cartridge containing vaporizable material to a power-supplying device. The connector may include a housing having electrical contacts, a cartridge-receiving end for receiving a conductive end of the cartridge, and a flexible, preferably silicone, ring connected to the cartridge-receiving end of the housing for retaining the conductive end of the cartridge inserted therethrough against the electrical contacts. The electrical contacts of the housing may thus include a positive electrical contact disposed in and through the housing having a first end and a second end that electrically connects to a positive contact within the conductive end of the cartridge, and at least one ground contact disposed in and through the housing having a first end and a second end that connects to a grounding area, such as the 510-threading of a 510 cartridge, on the conductive end of the cartridge.

In one preferred implementation, the second end of the positive electrical contact may comprise spring steel which is shaped to flexibly compress when a force is applied against it, such as a force applied by the positive contact of the cartridge, and to substantially return to its original shape when the cartridge is removed from the power-supplying device.

In the present invention, the housing may preferably be installed and fixed in a cartridge-receiving compartment of the power supplying device, such that a pen-shaped cartridge, such as a conventional 510 cartridge, can easily be inserted in (e.g., slid into) the cartridge-receiving compartment and snapped into the housing and retained by a flexible ring.

Moreover, in one preferred embodiment, the connector of the present invention includes a non-conductive, flexible, preferably silicone, boot having a first open end, a second open end and a cavity. This cavity snuggly encases or houses the housing, and the flexible ring may be integral with the boot at its second end. Further, the boot's first open end may comprise an air inlet port for drawing air in and through the housing. The boot may further include a sensor-receiving opening adapted to receive a sensor, such as a pressure sensor that senses the air flow passing from the air inlet port to the second open end.

In yet further detail, the second end of the positive electrical contact may terminate in an electrically conductive dome that contacts the positive contact of the cartridge. This can assist in ensuring good electrical contact for any of a variety of cartridge designs. Moreover, the present invention can be ideally suited for power-supplying systems that are activated by negative air pressure sensed by the user drawing on the cartridge connected to the system. Thus, preferably, this dome is designed with a central hole for allowing air flow passing through the housing to flow therethrough.

The silicon boot may further includes a first slit for extending the first end of the positive electrical contact therethrough and a second slit for extending the first end of the ground electrical contact therethrough.

In another embodiment, the present invention discloses a power supplying system for use with a cartridge containing vaporizable material. The system may include a circuit board containing a heater circuit, a power source electrically connected to the circuit board; an activator that activates the heater circuit; and a push-connect connector for removably connecting a vape cartridge thereto. This connector is designed with any combinations of features and structures described above.

The present invention also discloses a method for simply and repeatedly removably push-connecting a cartridge, such as a 510-vape cartridge, to a power-supplying device, or battery unit. This method may comprise sliding, or inserting, the electrically conductive end of the cartridge—and in the case of the 510 cartridge, the threaded end—into a cartridge-receiving chamber of the device and then pushing the cartridge into the chamber such that conductive end of the vaporizable material cartridge passes through an opening defined by a flexible, preferably silicone, ring disposed on a cartridge-receiving housing, tending to create a firm, inward retention force and good electrical positive and ground connection.

It is to be understood that the invention is not limited in its application to the details of construction and the arrangement of components described hereinafter and illustrated in the drawings and photographs. Those skilled in the art will recognize that various modifications can be made without departing from the scope of the invention.

BRIEF DESCRIPTION OF THE DRAWINGS

Further advantages of the present invention may become apparent to those skilled in the art with the benefit of the following detailed description of the preferred embodiments and upon reference to the accompanying drawings in which.

DETAILED DESCRIPTION OF THE PREFERRED EMBODIMENTS

Figure 1:
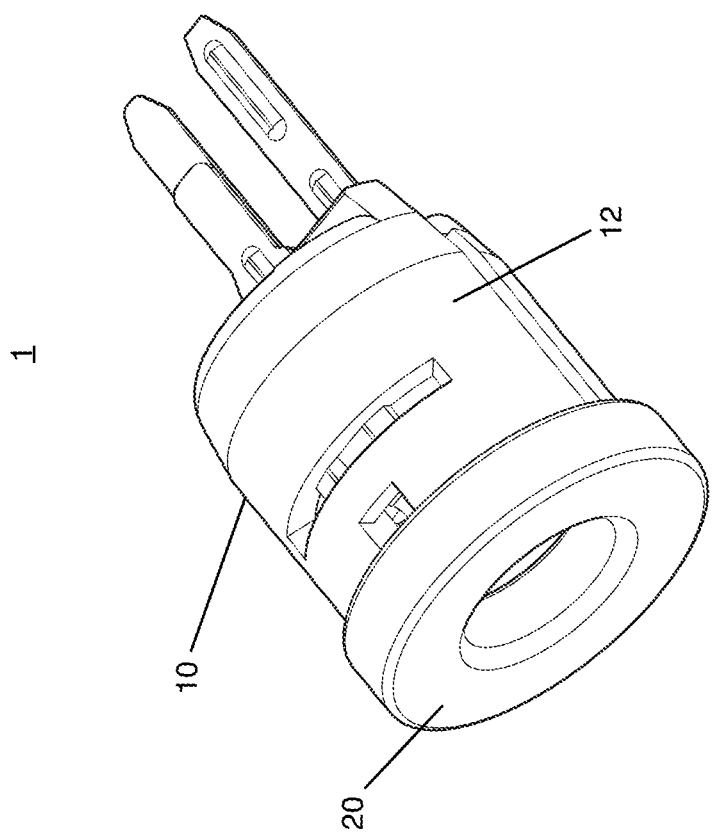
FIG. 1 is a perspective view of one non-limiting embodiment of the connector of the present invention.

Referring now to the drawings, like reference numerals designate identical or corresponding features throughout the several views.

Embodiments of the push-connector of the present invention are shown in FIGS. 1-4. As seen in FIG. 1, in a first embodiment, connector 1 comprises a housing assembly (or housing) 10 and a flexible ring 20 that may be attached to the open end of the housing. The housing 10 is preferably made of a generally cylindrical, hard, plastic body 12 that defines at one end an opening 14 (see, e.g., FIGS. 2(a) and 2(b)) into which a cartridge may be inserted. Flexible ring 20 may have an inner diameter that is smaller than both the inner diameter of the cartridge receiving opening 14 to which it is attached, and the outer diameters of the threaded and unthreaded parts of the end of any cartridge, such as a 510-thread cartridge, which may be inserted into the connector 1. This ring may be made from any robust, flexible material capable of withstanding repeated frictional, scraping forces on it caused by repeatedly inserting and removing cartridges from the connector, while maintaining its shape. In one preferred embodiment, the ring is made from silicone, and preferably medical-grade silicone.

Figure 2A:
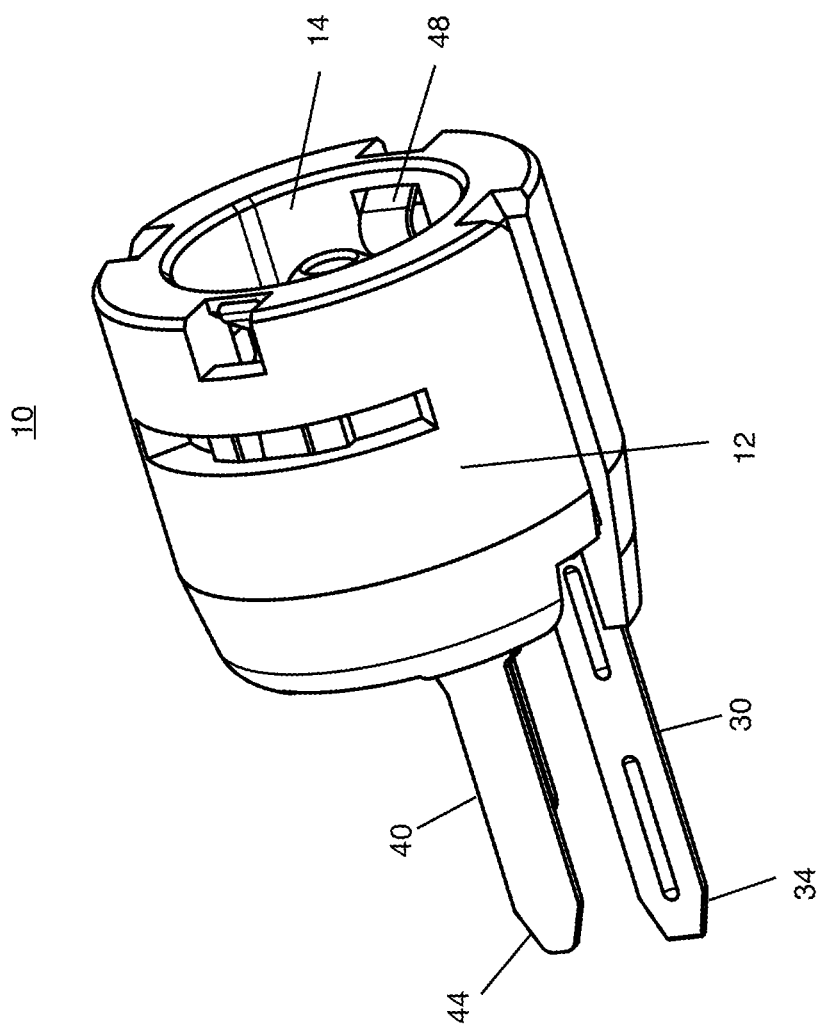
FIG. 2(a) is a perspective view of the housing of the connector shown in FIG. 1.
Figure 2B:
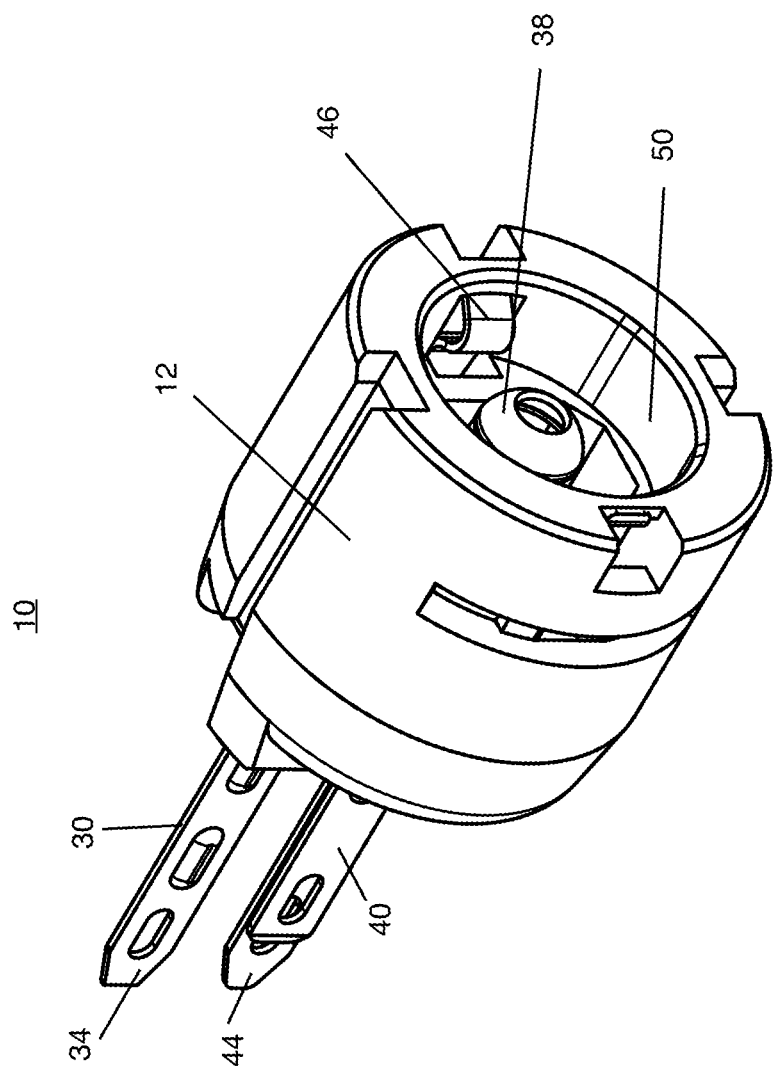
FIG. 2(b) is another perspective view of the housing shown in FIG. 2(a)
Figure 2C:
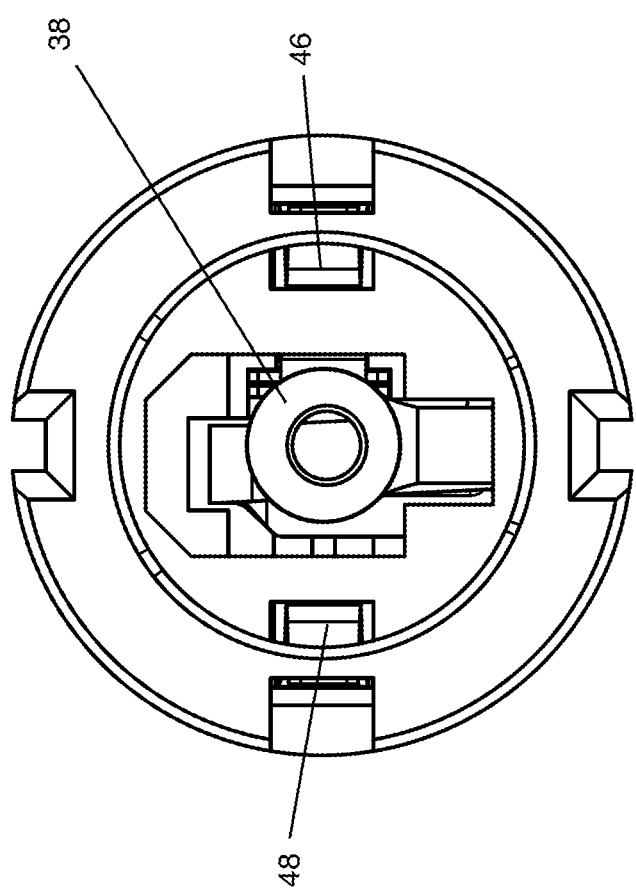
FIG. 2(c) is a plan top view of the housing shown FIG. 2(a)
Figure 3:
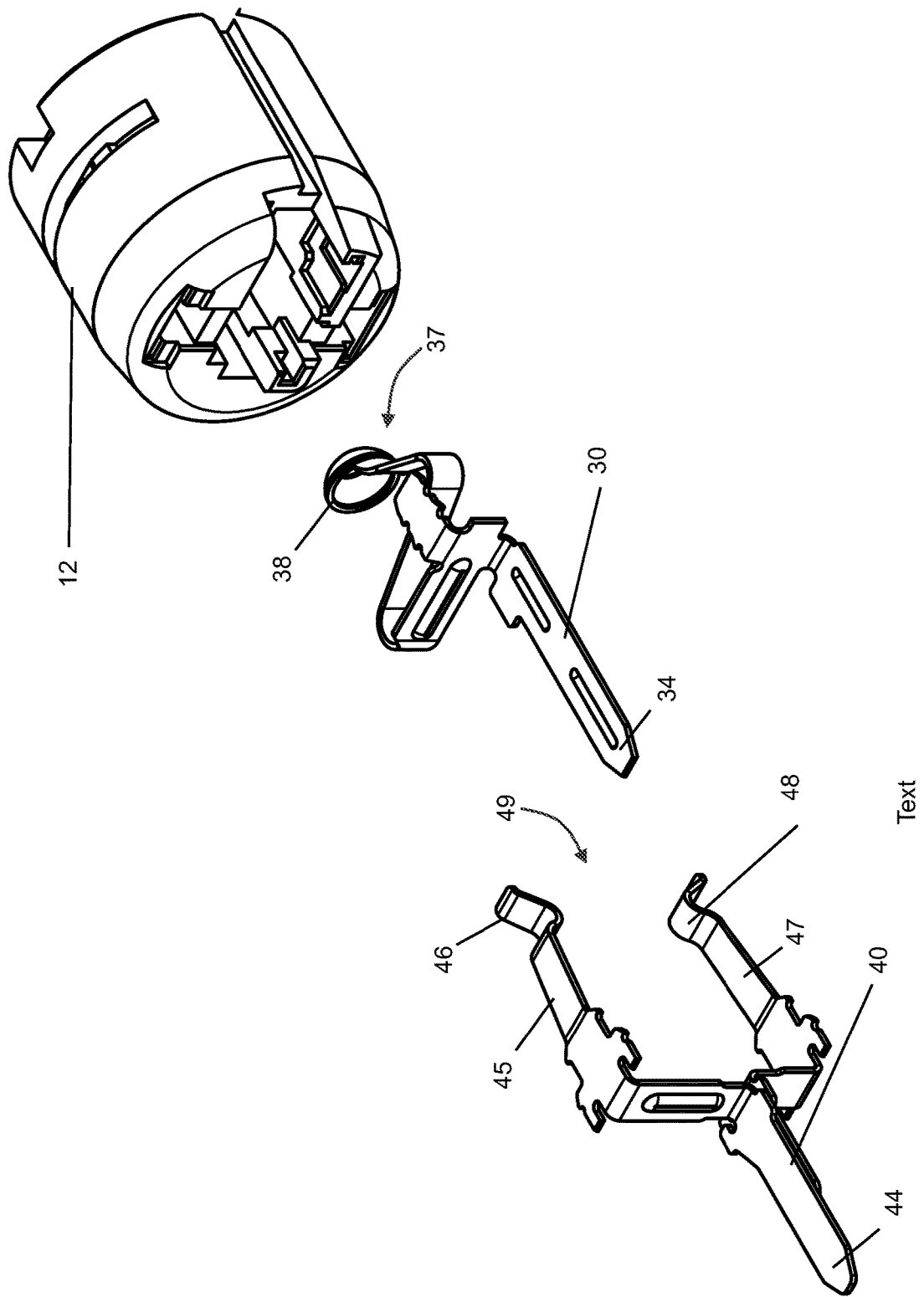
FIG. 3 is an exploded perspective view of the housing shown in FIGS. 2(a)-2(c)
Figure 4:
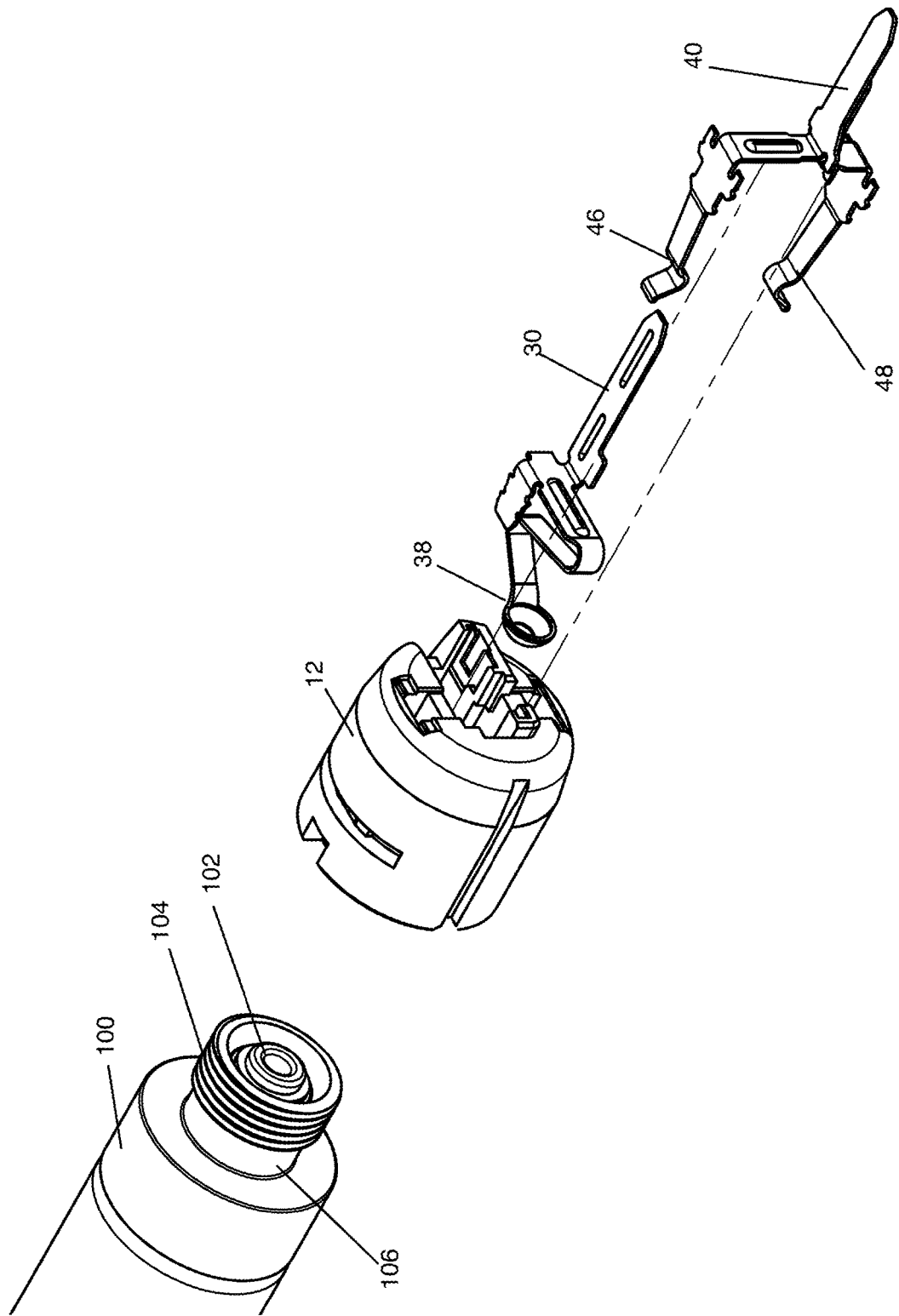
FIG. 4 is a second exploded perspective view of the housing shown in FIGS. 2(a)-2(c), together with a portion of an exemplary 510 cartridge in position to be push-connected onto the housing, in accordance with one non-limiting embodiment of the present invention.

Various views of housing assembly 10 of connector 1 of FIG. 1 are now shown and described in connection with FIGS. 2(a)-2(c), which show various views of an embodiment of housing assembly 10 as assembled, and with FIGS. 3 and 4 showing exploded perspective views of housing assembly 10. The housing 10 may comprise two main sets of components, namely hard body 12 and electrical contacts 30, 40 that are installed into body 12 during assembly. As seen, contact 30 may be a positive electrical contact having a first end 34 and a second end 37 that terminates in an electrically conductive dome 38 having a hole in or near its center. For example, referring to FIG. 6, the dome 38 may have a central hole 39 for allowing air flow 212 passing through the housing 10 to flow therethrough. Contact 40 may serve as the electrical ground having a first end 44 and a second end 49. In this preferred embodiment, as best seen in FIGS. 3 and 4, this ground contact 40 preferably splits off into two prongs 45 and 47, each terminating at the second end 49 in grounding pads 46 and 48, respectively. It is understood that in other embodiments, one prong or more than two prongs may be used. As will be further explained, when finally assembled in a power supplying device, the first ends or prongs 34 and 44 of positive and ground electrical contacts 30 and 40 respectively are physically and electrically connected to the power supply system of the battery.

As best seen in the exploded perspective views of FIGS. 3 and 4, during assembly, the positive contact 30 is inserted through the middle of body 12 and prongs 45 and 47 of ground contact 40 are inserted into openings of body 12. Thus, in this embodiment, the assembled housing has grounding pads 46 and 48 protruding from the inner walls of the body 12 (see FIG. 2(c)), in position to physically and electrically contact the threads 104 of a cartridge 100 that may be inserted therein (of course, after full assembly of the connector in a battery or power supply). Moreover, once fully assembled, dome 38 of positive contact 30 will be in position to make physical and electrical contact with the positive pin 102 of cartridge 100.

Thus, once connector 1 is fully assembled together and into a battery or power supply device, all the user needs to do is push the threaded end of a cartridge, such as 510 cartridge 100, through the silicone ring 20 and into the housing 10, thereby simultaneously making good positive and ground electrical connections, while the flexible ring 20 firmly holds and seals the neck 106 near the connection end of the 510 cartridge 100 to it. To remove a cartridge, the user simply pulls it off the connector of the power-supplying device, much the same way a magnetically-connected system operates. However, it can be readily appreciated that this design can be simpler to use than the conventional 510 screw solution and any of the newer "improved" designs described above. The design of the present invention thus preferably eliminates the need (a) for users to screw the cartridge to the battery; (b) any additional parts such as adapters; and (c) for esoteric and costly magnetic solutions.

Focusing now on the electrical contacts, in preferred embodiments and as best seen in FIGS. 3 and 4, positive contact 30 is designed preferably using a "spring metal" material and shaped as seen, such that when assembled through opening 50 of the housing 10 (FIG. 2(c)), its domed end 38 can vertically flex. Thus, when pushing or snapping a cartridge in the housing of the connector, the cartridge's positive pin 102 will always make secure contact with this positive contact. Likewise, when ground contact 40 is assembled into the body 12, the nubs 46 and 48 may likewise be biased slightly inwardly, such that when any cartridge is pushed into the device, the nubs can flex but are sure to press firmly against and make good electrical contact with the outer 510 thread 104, which serves as the ground of the cartridge. Finally, the opposite end prongs 34 and 44 of positive and ground electrical contacts 30 and 40 respectively may extend out the back end of device. These ends are physically electrically connected to the power supply system of the battery and is understood by those skilled in the art.

As seen in these embodiments, the positive and ground electrical contact design can serve as a helpful advance for the field because it may solve, or at least substantially reduce, the problem of premature battery failure caused by liquid leakage as described above in connection with prior art designs. With this design, even if a cartridge leaks some liquid into the battery, it likely won't matter for the electrical connection, because ends 38, 46 and 48 are positioned in cavity 50 relatively far from the base of the battery connector, and should thus make good electrical contact with the cartridge irrespective of leakage.

Figure 5A:
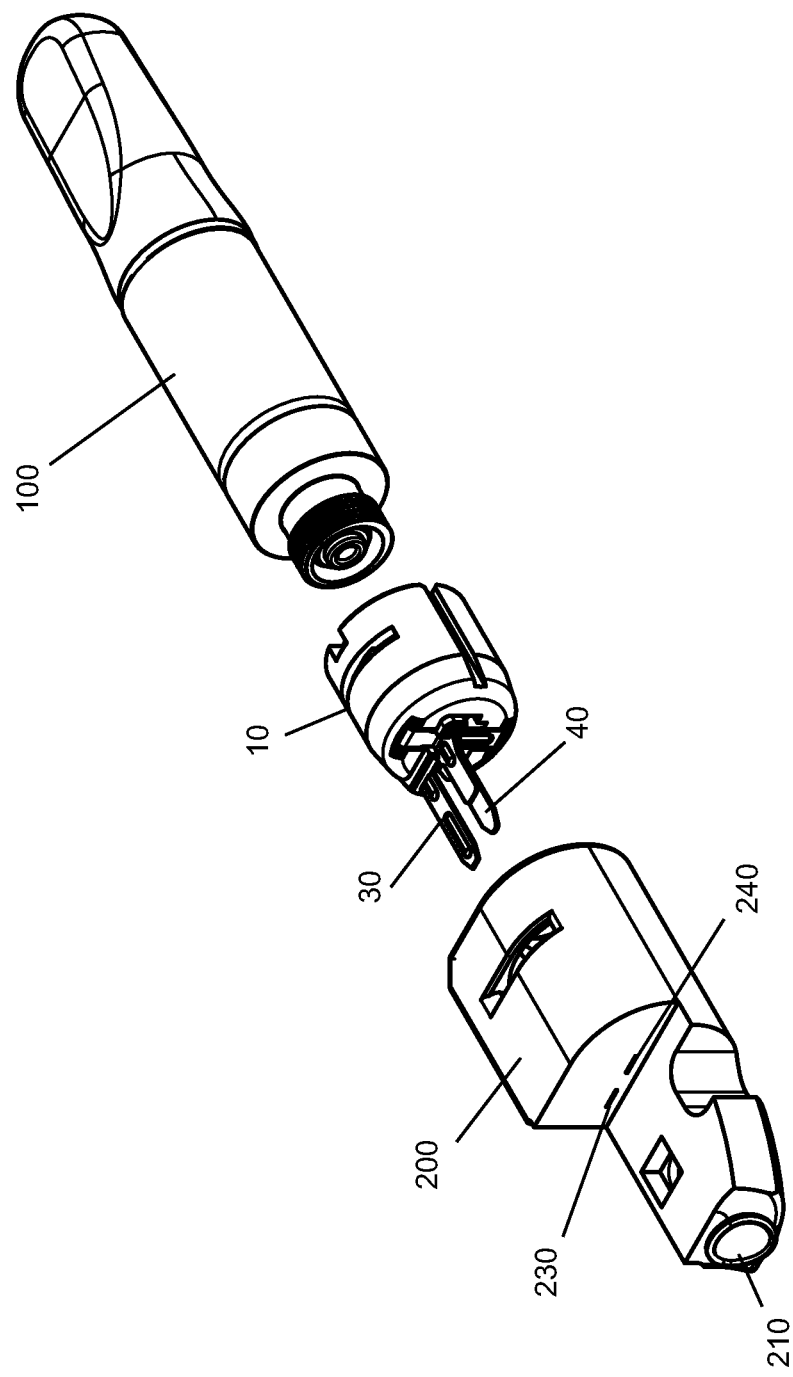
FIG. 5(a) is an exploded perspective view of another embodiment of the present invention showing a housing-in-boot implementation, with a 510-cartridge ready to be inserted into the system.
Figure 5B:
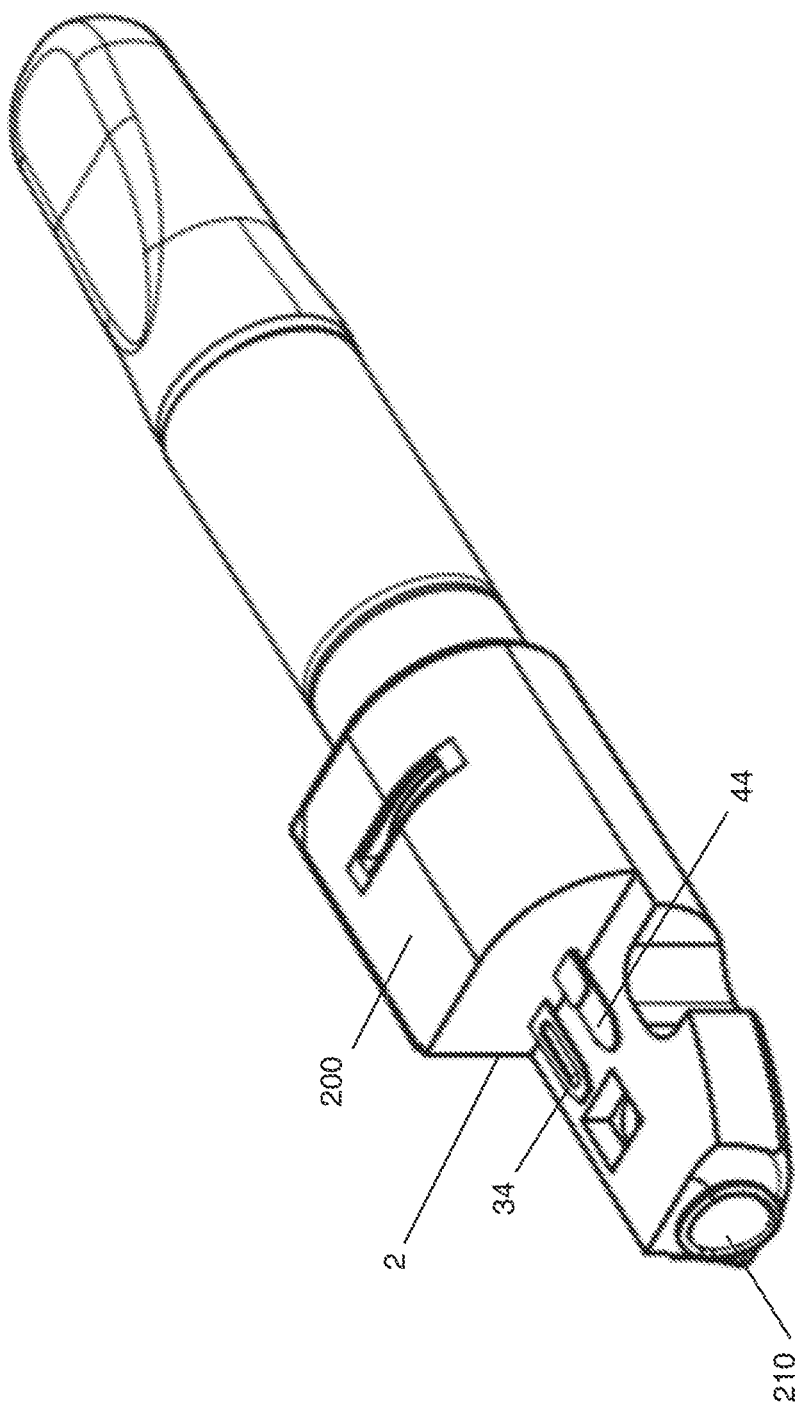
FIG. 5(b) is an assembled perspective view of the system shown in FIG. 5(a) with a cartridge push-connected therein.
Figure 6:
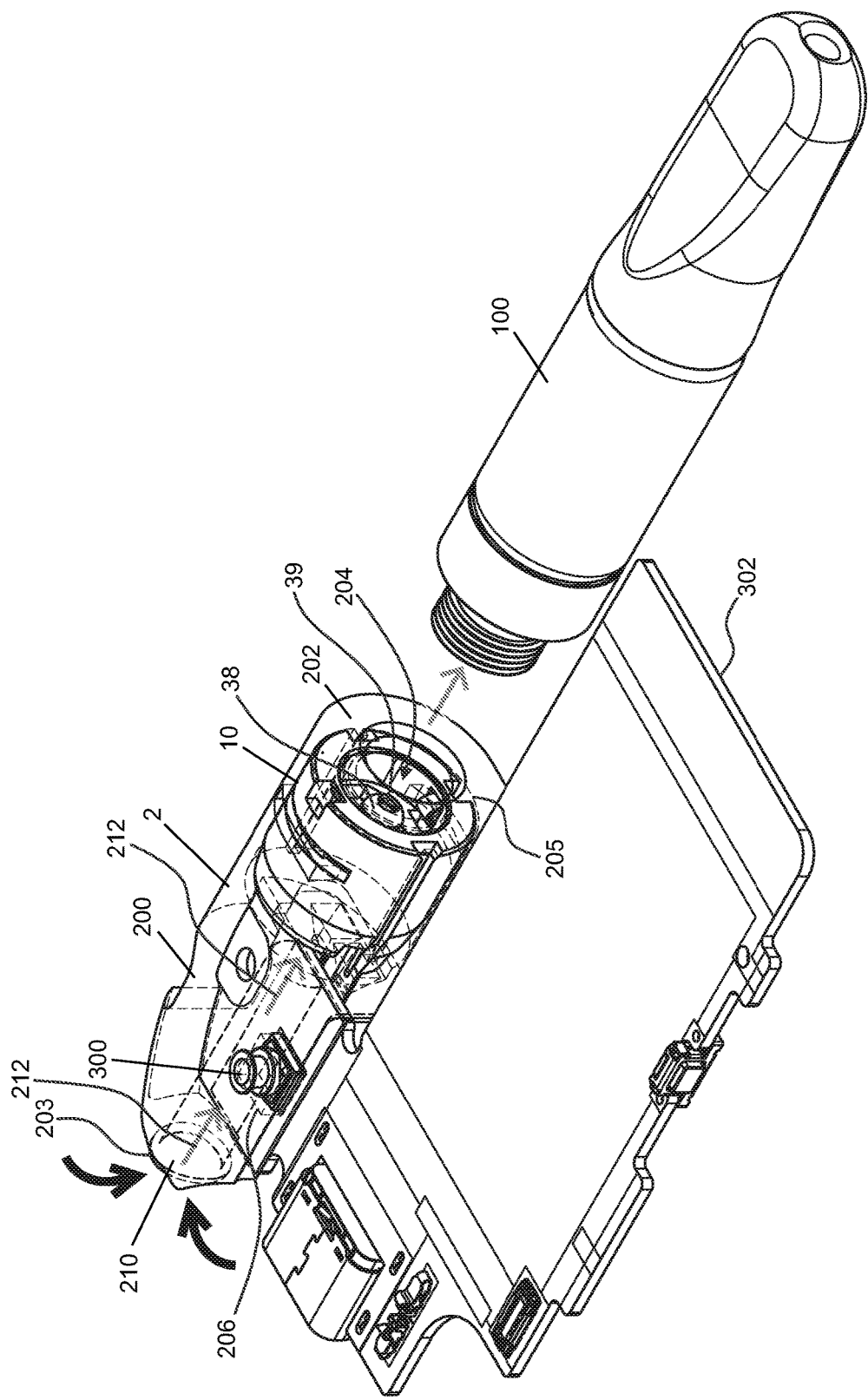
FIG. 6 is a perspective, partial see-through view of the connector shown in FIGS. 5(a) and 5(b), as assembled to a PCB board of a power-supplying device, and a cartridge in position to be push-connected into the connector.
Figure 7:
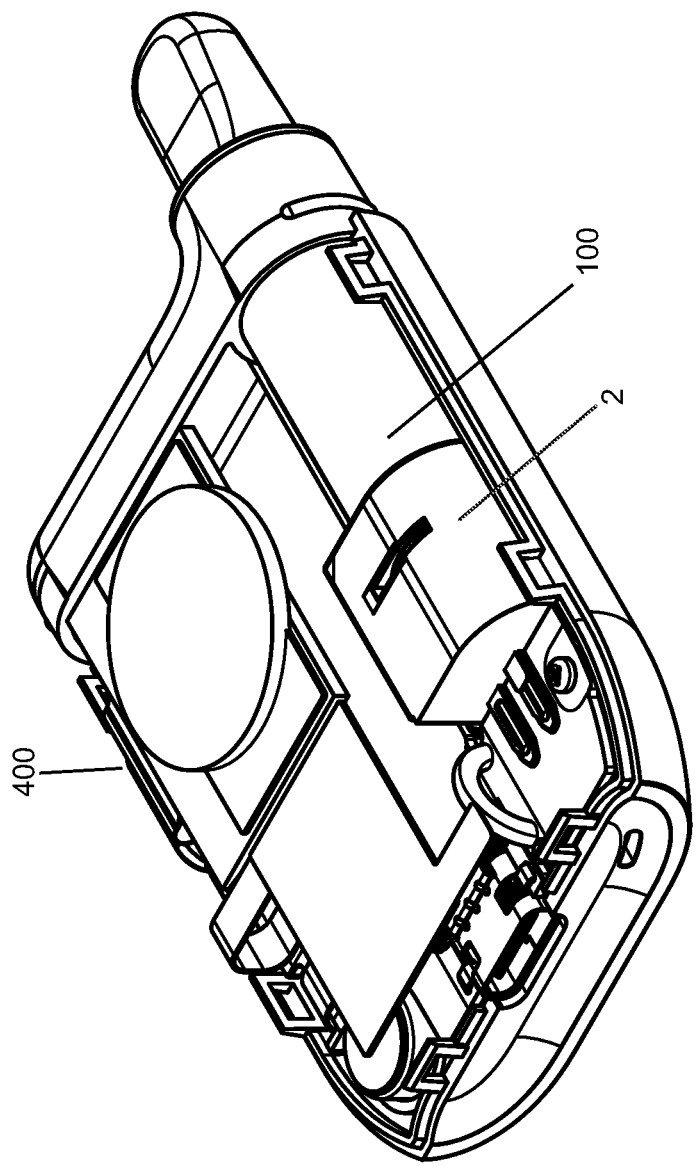
FIG. 7 is a perspective view of a fully assembled power-supplying device designed with the inventive connector shown in FIGS. 5(a) and 5(b), with a protective cover removed, shown with a cartridge inserted into the connector.

An alternative embodiment of the present invention is shown in exploded view FIG. 5(a), assembled view shown in FIG. 5(b), and FIGS. 6 and 7. In this embodiment, the inventive connector 2 comprises a hard shell housing 10 similar to the one described above. Replacing the ring 20 in the prior embodiment, however, is a flexible, preferably silicone, boot 200 which completely or substantially encompasses the body of the housing within a cavity 205 that houses the housing 10. As best seen in FIG. 6, the see-through view of the inventive connector as attached to a PCB board (circuit board) 302 of a power-supplying device, boot 200 may serve as an electrically isolating protective sleeve to body 12, such that the housing 10 is installed in the cartridge receiving compartment 204. The boot is also preferably molded with a cartridge-receiving end (i.e., a second open end) 202 that serves the same function of the ring 20 in the embodiment shown in FIG. 1. Turning back to FIGS. 5(a) and 5(b), during assembly, housing 10 completely slides into boot 200 until prongs 34 and 44 slide through slits 230 and 240 cut in the boot, respectively. Moreover, in this embodiment, boot 200 preferably includes an aperture (i.e., air inlet port) 210 at the first open end 203, which is the end opposite the cartridge-receiving end (i.e., second open end) 202. This end may be in air-fluid contact with a pressure sensor (activator) 300 seen in FIG. 6 that activates the power supply when it senses a user drawing on a cartridge that is connected to the battery. For example, the boot 200 may further include a sensor-receiving opening 206 adapted to receive a sensor 300 that senses the air flow 212 passing from the air inlet port 210 to the second open end 202. Accordingly. FIG. 7 shows this connector 2 installed in a power-supplying device 400 shown here with its cover removed, and a cartridge 100 push-connected thereto.

Figure 8:
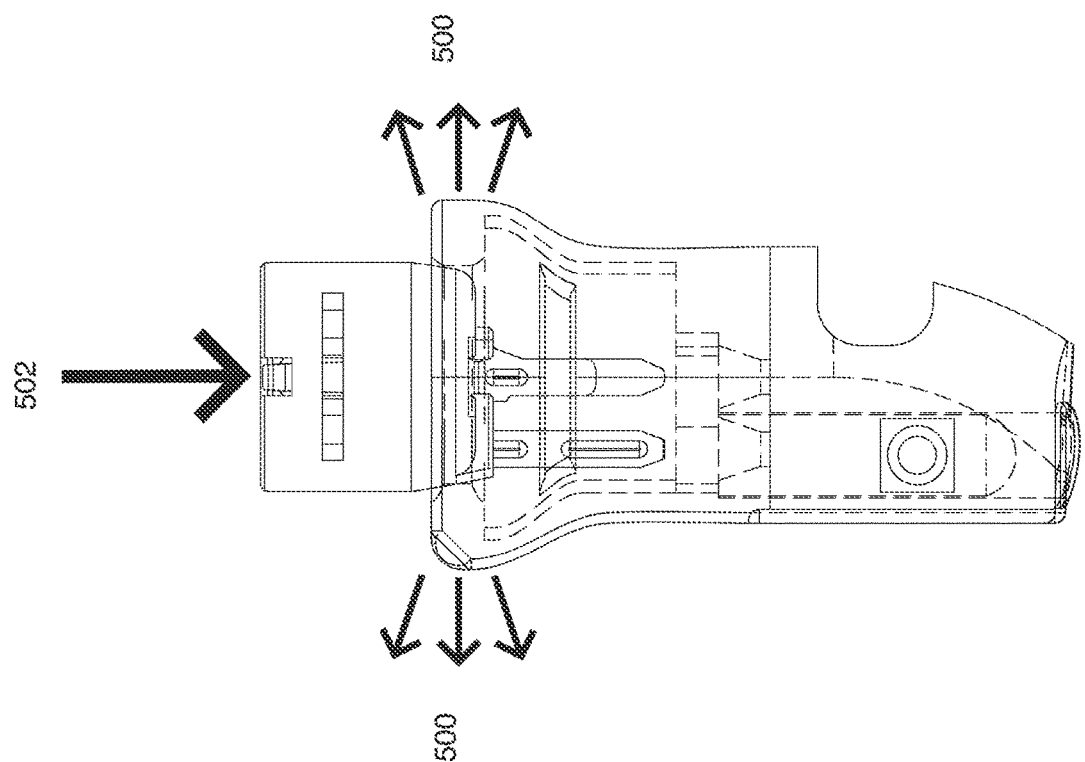
FIG. 8 shows a method of assembling one embodiment of the connector of the present invention.

Assembling the housing 10 into the silicone boot 200 of this embodiment will typically require a tool. Thus, as seen in FIG. 8, the cartridge receiving end of the boot will preferably be stretched in a uniformly outward direction as shown by arrows 500. Then, the housing 10 may be inserted in the boot, as shown by arrow 502.

While embodiments of the invention have been illustrated and described, it is not intended that these embodiments illustrate and describe all possible forms of the invention. Various changes, modifications, and alterations in the teachings of the present invention may be contemplated by those skilled in the art without departing from the intended spirit and scope thereof. It is intended that the present invention encompass such changes and modifications.

What is claimed is:

1. A connector for push-connecting a cartridge containing vaporizable material to a power-supplying device, the connector comprising:
   a. a housing having electrical contacts and a cartridge-receiving end for receiving a conductive end of the cartridge; and
   b. a flexible ring connected to the cartridge-receiving end of the housing for retaining the conductive end of the cartridge against the electrical contacts.

2. The connector of claim 1, wherein the electrical contacts include:
   a. a positive electrical contact disposed in and through the housing having a first end and a second end that electrically connects to a positive contact within the conductive end of the cartridge; and
   b. a ground contact disposed in and through the housing, the ground contact having a first end and a second end that connects to a grounding area on the conductive end of the cartridge.

3. The connector of claim 2, wherein the second end of the positive electrical contact comprises spring steel and is shaped to flexibly compress when a force is applied against the second end by the positive contact of the cartridge and substantially return to the second end's original shape when the cartridge is removed from the power-supplying device.

4. The connector of claim 2, wherein the housing is installed in a cartridge-receiving compartment of the power supplying device.

5. The connector of claim 2, further including a non-conductive, flexible silicone boot having a first open end, a second open end and a cavity that houses the housing, and wherein the flexible ring is integral with the boot at its second end.

6. The connector of claim 5, wherein the first open end of the boot comprises an air inlet port for drawing air in and through the housing.

7. The connector of claim 6, wherein the boot further includes a sensor-receiving opening adapted to receive a sensor that senses the air flow passing from the air inlet port to the second open end.

8. The connector of claim 7, wherein the sensor is a pressure sensor.

9. The connector of claim 2, wherein the second end of the positive electrical contact terminates in an electrically conductive dome that contacts the positive contact of the cartridge.

10. The connector of claim 9, wherein the dome has a central hole for allowing air flow passing through the housing to flow therethrough.

11. The connector of claim 7, wherein the boot further includes a first slit for extending the first end of the positive electrical contact therethrough and a second slit for extending the first end of the ground electrical contact therethrough.

12. The connector of claim 2, wherein the cartridge is a 510 cartridge and the second end of the ground contact is adapted to contact the threading of the 510 cartridge.

13. A power supplying system for a cartridge containing vaporizable material, the system comprising:
  a. circuit board containing a heater circuit;
  b. a power source electrically connected to the circuit board;
  c. an activator that activate the heater circuit; and
  d. a push-connect connector for removably connecting the cartridge thereto, the connector comprising
    i. a housing having a positive electrical contact and a ground electrical contact, both electrically-connected to the circuit board, and a cartridge-receiving end for receiving a conductive end of the cartridge; and
    ii. a non-conductive, flexible silicone boot having a first open end, a second open end and a cavity that houses the housing, the boot including a flexible ring at the second open end for retaining the conductive end of the cartridge inserted therein against the electrical contacts.

14. The system of claim 13, wherein the positive electrical contact of the housing comprises spring steel and terminates in an electrically-conductive dome for contacting the positive pin of the cartridge when the cartridge is inserted in the second open end, and the ground electrical contact of the housing terminates in a nub for electrically contacting the threads of the cartridge when the cartridge is inserted in the second open end.

15. The system of claim 14, wherein the first open end of the boot comprises an air inlet port for drawing air in and through the housing and the dome includes a central hole for providing a path for the air to be drawn into the cartridge when the cartridge is inserted in the second open end and a user draws on the cartridge.

16. A method for removably connecting a 510 cartridge containing vaporizable material to a power-supplying device, the method comprising:
  a. sliding the threaded end of the 510 cartridge into a chamber of the power-supplying device; and
  b. pushing the threaded end of the 510 cartridge through a silicone ring opening, creating a firm inward retention force.

\* \* \* \* \*